(12) United States Patent
Zandi et al.

(10) Patent No.: US 10,064,637 B2
(45) Date of Patent: Sep. 4, 2018

(54) CATHETER-BASED APPARATUSES AND METHODS

(71) Applicant: Transverse Medical, Inc., Golden, CO (US)

(72) Inventors: Abdolrahim Zandi, Laguna Niguel, CA (US); Sepehr Fariabi, Newport Coast, CA (US); J. Eric Goslau, Evergreen, CO (US); David S. Nevrla, Friends wood, TX (US); Brad Lees, Sammamish, WA (US)

(73) Assignee: Transverse Medical, INC, Golden, CO (US)

( * ) Notice: Subject to any disclaimer, the term of this patent is extended or adjusted under 35 U.S.C. 154(b) by 0 days.

(21) Appl. No.: 15/122,589

(22) PCT Filed: Oct. 9, 2015

(86) PCT No.: PCT/US2015/054954
§ 371 (c)(1),
(2) Date: Aug. 30, 2016

(87) PCT Pub. No.: WO2017/062036
PCT Pub. Date: Apr. 13, 2017

(65) Prior Publication Data
US 2017/0143356 A1 May 25, 2017

(51) Int. Cl.
*A61B 17/221* (2006.01)
*A61B 17/12* (2006.01)
*A61B 17/00* (2006.01)

(52) U.S. Cl.
CPC ........ *A61B 17/221* (2013.01); *A61B 17/1204* (2013.01); *A61B 17/12109* (2013.01);
(Continued)

(58) Field of Classification Search
CPC .................. A61F 2/01; A61F 2002/011; A61F 2002/016; A61B 17/12022;
(Continued)

(56) References Cited

U.S. PATENT DOCUMENTS 7,785,343 B2 * 8/2010 Johnson .................... A61F 2/01
606/200
8,114,114 B2 2/2012 Belson
(Continued)

FOREIGN PATENT DOCUMENTS

DE  20 2009 018 975.9 U1  6/2015
DE  20 2009 018 976.7 U1  6/2015
(Continued)

*Primary Examiner* — Shaun L David
(74) *Attorney, Agent, or Firm* — Crawford Maunu PLLC

(57) ABSTRACT

As may be implemented with various aspects of the present disclosure, a mesh structure is coupled to inner and outer frames that operate with struts to apply pressure to the mesh. Such an approach may involve sealing the mesh around an opening, such as around one or more artery openings along an interior wall of vascular tissue (e.g., in an aortic arch). Accordingly, blood flow can be filtered in a manner that is useful for capturing particulates such as those resulting from surgical operations. In various implementations, the mesh, struts and frames are deployed using a catheter and shaft coupled to the frames. Such an approach can be implemented to apply a spring force from the shaft and through the frames for sealing the mesh.

18 Claims, 12 Drawing Sheets

(52) U.S. Cl.
CPC ............... *A61B 17/12172* (2013.01); *A61B 2017/00526* (2013.01); *A61B 2017/00955* (2013.01); *A61B 2017/2215* (2013.01)

(58) Field of Classification Search
CPC .......... A61B 17/12027; A61B 17/1204; A61B 17/12099; A61B 17/12109; A61B 17/12113; A61B 17/12122; A61B 17/12168; A61B 17/12172; A61B 17/12178; A61B 17/221; A61B 2017/2212; A61B 2017/2215; A61B 2017/2217
See application file for complete search history.

(56) References Cited

U.S. PATENT DOCUMENTS

| | | | |
|---|---|---|---|
| 8,308,754 | B2 | 11/2012 | Belson |
| 8,414,482 | B2 | 4/2013 | Belson |
| 8,430,904 | B2 | 4/2013 | Belson |
| 8,679,149 | B2 | 3/2014 | Belson |
| 8,728,114 | B2 | 5/2014 | Belson |
| 9,107,734 | B2 | 8/2015 | Belson |
| 2002/0123761 | A1 | 9/2002 | Barbut et al. |
| 2002/0161394 | A1 | 10/2002 | Macoviak et al. |
| 2006/0129051 | A1 | 6/2006 | Rowe et al. |
| 2010/0324589 | A1* | 12/2010 | Carpenter ........ A61B 17/12022 606/200 |
| 2011/0295304 | A1* | 12/2011 | Jonsson ............ A61F 2/01 606/200 |
| 2013/0103075 | A1* | 4/2013 | Wang ................ A61F 2/01 606/200 |
| 2013/0123835 | A1* | 5/2013 | Anderson ........ A61F 2/00 606/200 |
| 2014/0074148 | A1* | 3/2014 | Glenn .............. A61F 2/013 606/200 |
| 2014/0243880 | A1 | 8/2014 | Schotzko et al. |
| 2014/0243881 | A1 | 8/2014 | Lees et al. |
| 2016/0262864 | A1* | 9/2016 | Von Mangoldt ........ A61F 2/013 |
| 2016/0324621 | A1* | 11/2016 | Shezifi ............ A61F 2/01 |

FOREIGN PATENT DOCUMENTS

| | | |
|---|---|---|
| DE | 20 2009 018 977.5 U1 | 6/2015 |
| DE | 20 2009 018 998.8 U1 | 6/2015 |
| DE | 20 2009 018 999.6 U1 | 6/2015 |
| DE | 20 2009 019 000.5 U1 | 6/2015 |
| DE | 20 2009 019 019.6 U1 | 9/2015 |
| EP | 2 337 521 B3 | 7/2015 |
| EP | 20535 018 B1 | 10/2015 |
| EP | 2 537 488 B1 | 4/2016 |
| EP | 2 837 360 B1 | 7/2016 |
| EP | 2 537 489 B1 | 11/2016 |
| WO | 2010026240 A1 | 3/2010 |
| WO | WO 2014076219 A1 * | 5/2014 ............ A61F 2/013 |

* cited by examiner

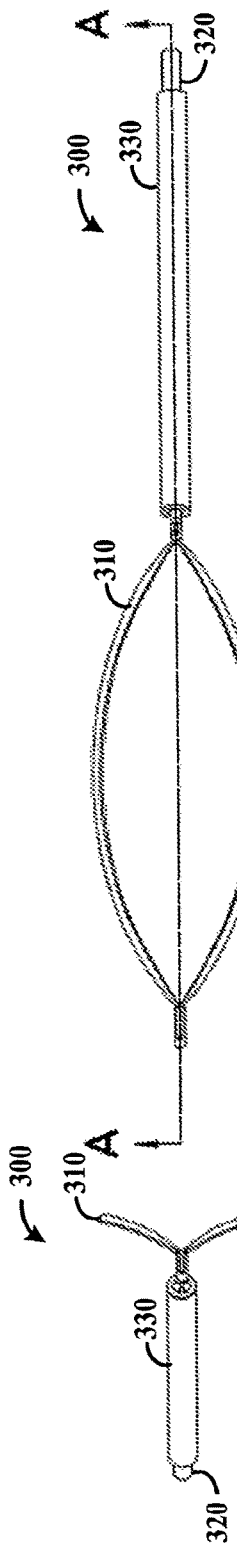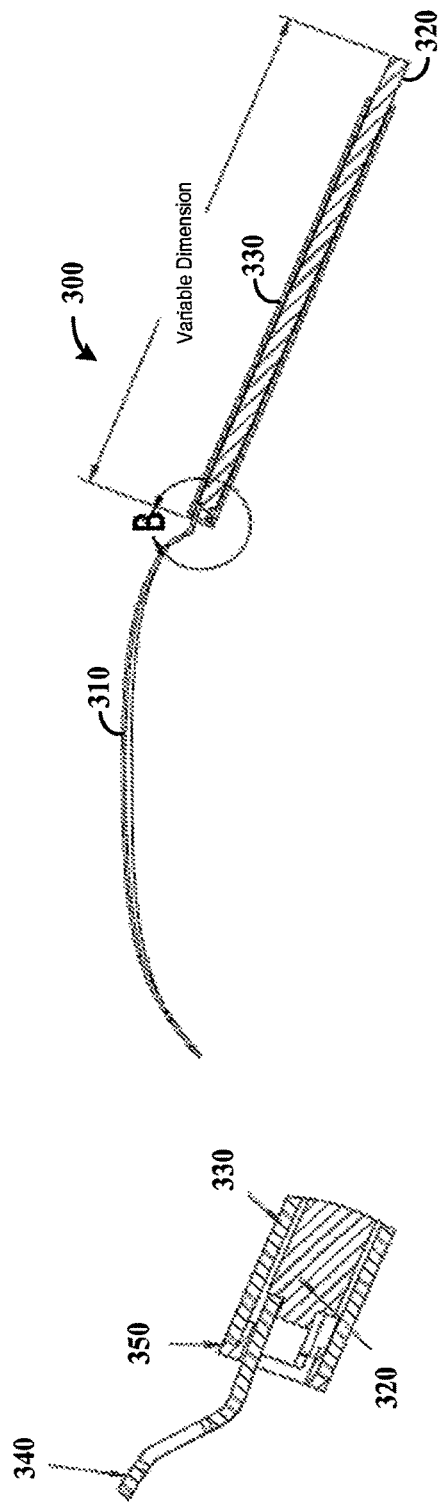

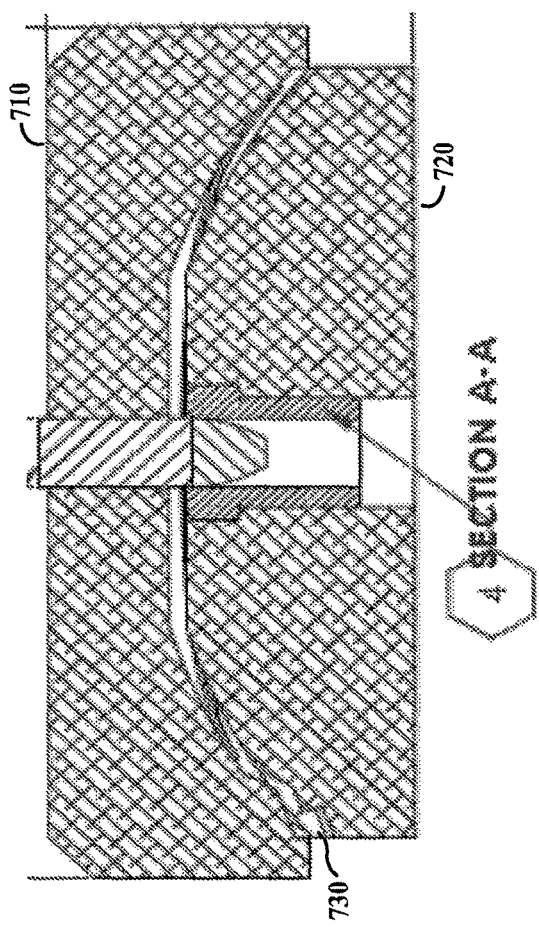
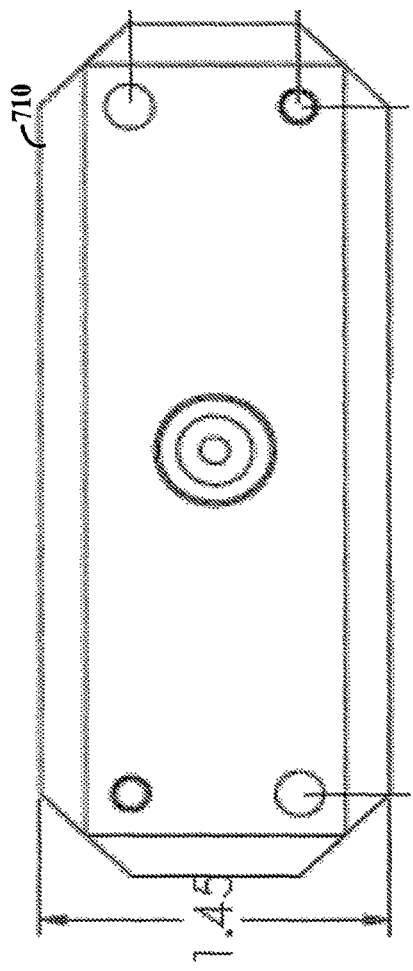
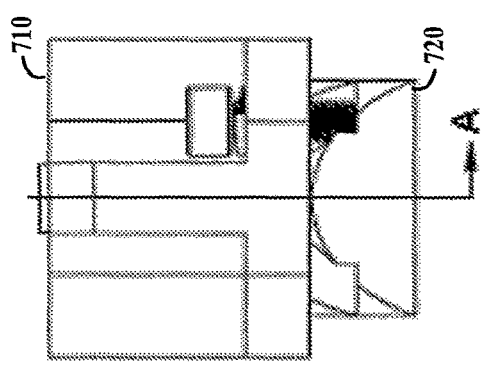
FIG. 7B
FIG. 7C

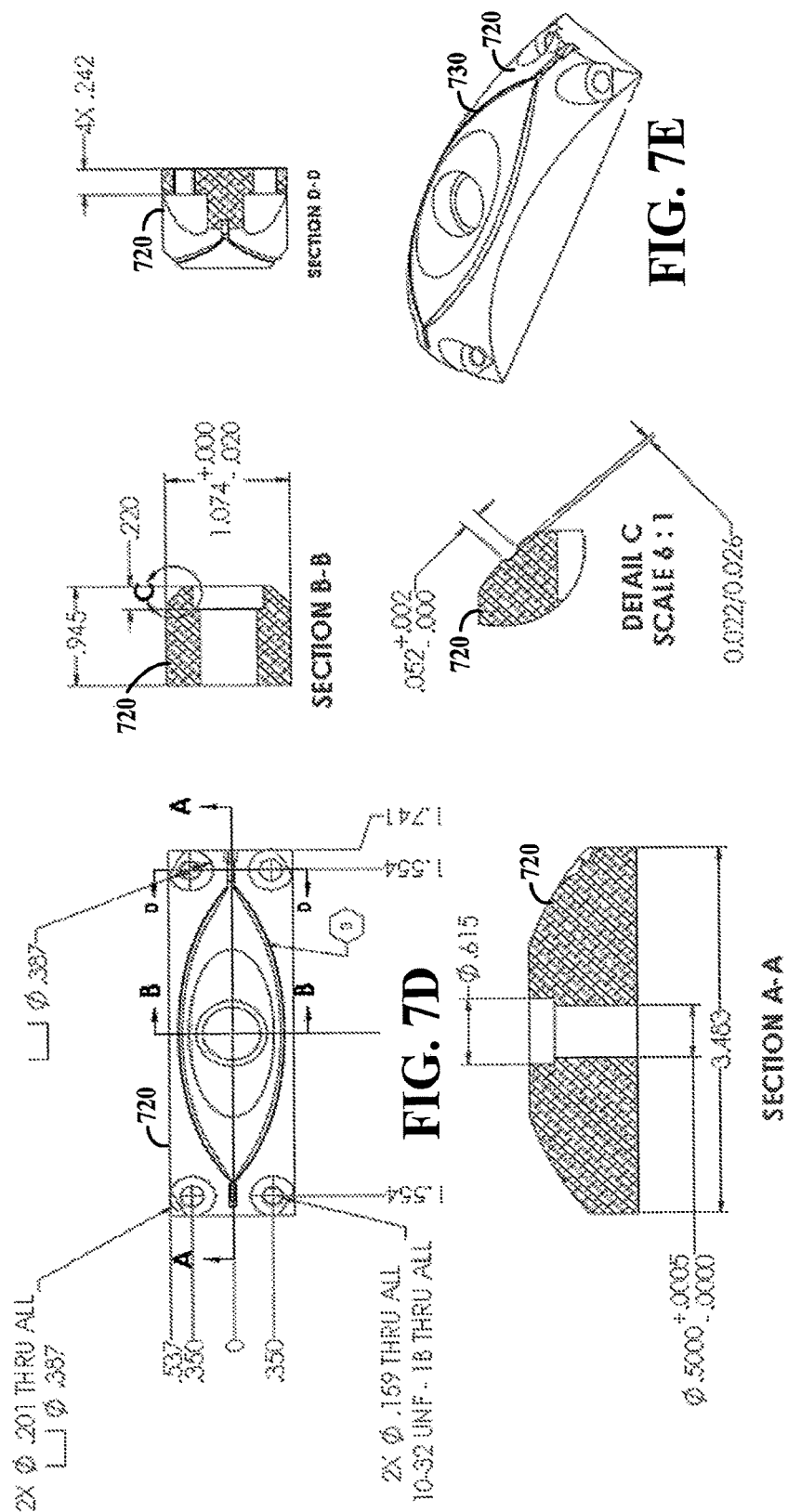

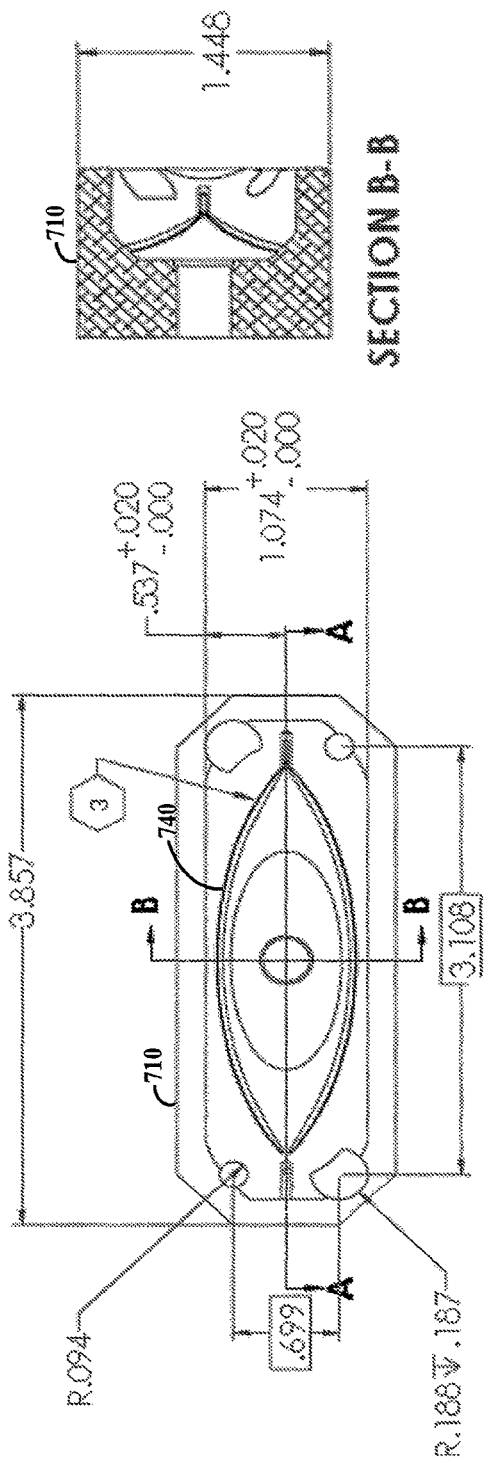
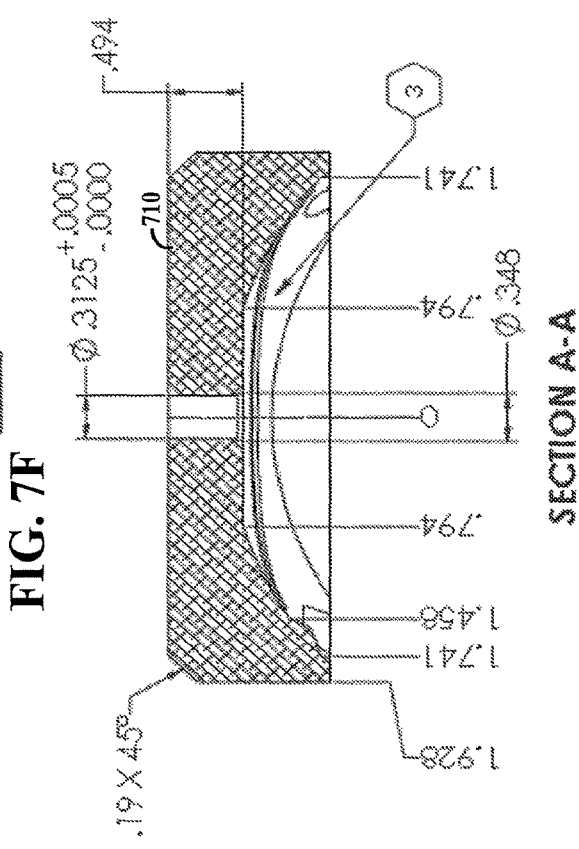
FIG. 7F
FIG. 7G

CATHETER-BASED APPARATUSES AND METHODS

FIELD

Aspects of various embodiments are directed to catheter-based apparatuses and methods therefor.

BACKGROUND

Various treatments can be useful for treating a variety of medical conditions, such as coronary heart disease, aneurism and others. These treatments can often involve intervention with tissue, such as to remove, repair or otherwise treat tissue. For instance, coronary heart disease can sometimes involve heart valve disorders, which can be addressed via intervention techniques in which valves are repaired or replaced.

One manner that has been useful for treating various conditions involves the use of a catheter to enter a patient's arteries and provide access for a variety of techniques. For instance, various procedures can be performed via catheters, such as to repair or remove tissue, or to implant tissue or other devices. One such approach for addressing heart disease involves transcatheter-aortic valve replacement or implementation therapies (TAVR/TAVI). These and other trans-vascular approaches may involve the delivery of artificial or animal flaps/valves to a patient's heart via catheters.

While many treatment approaches have been useful, there have been many challenges to their safe implementation. It is common to introduce, cross and exchange a variety of percutaneous devices such as guide wires, catheters, sheaths, guide catheters, and adjunctive technologies to gain access to and treat a coronary vessel, coronary valve, or other vascular anatomy. These and other approaches to the repair or replacement of tissue can dislodge particles/debris (emboli) which are freed (released) from the vessel walls and structures causing uncontrolled and unprotected floating emboli to move freely. This freed emboli, and freely floating and uncontrolled emboli can be carried distally (away) via the blood stream and cause issues, such as by blocking or occluding coronary, peripheral, and neurovascular vessels. For instance, during the (TAVR/TAVI) procedure, native tissue can be compressed into the aorta wall to make room for replacement devices. This action may cause dislodging or displacement of arterial plaque, calcium, or thrombus as the devices transverse the aortic arch. These particles can have adverse effects, such as by causing a stroke. These and other matters have presented challenges to a variety of treatment approaches.

SUMMARY

Various example embodiments are directed to catheter-based apparatuses and their implementation.

According to an example embodiment, an apparatus includes a catheter extending from a proximal end to a distal end, a shaft within and operable to move in the catheter, and a filter component that is connected to the shaft and operable to retract within the distal end of the catheter. The filter component includes a mesh and inner and outer frames connected by struts. A perimeter of the mesh is coupled to the inner frame (and in some instances, to the outer frame), with the inner and outer frame extending along one another. The struts operate to apply a force between the outer frame and the inner frame, such as by applying a force that applies the inner frame and mesh against tissue (e.g., within vascular tissue).

Another embodiment is directed to a method as follows. A filter component is deployed from within a catheter, in which the filter component has inner and outer frames coupled by struts with a mesh coupled to a perimeter of the inner frame. The filter component is deployed by manipulating a shaft that extends from a proximal end of the catheter toward a distal end of the catheter, with the filter component coupled to a distal end of the shaft. A force that seals the mesh to an inner tissue wall is applied by manipulating the shaft and using the outer frame and struts to direct the force against the inner frame and the mesh.

In various implementations, the catheter is inserted into a human aortic arch and the filter component is deployed over at least one artery opening in the aortic arch. The mesh is sealed to a portion of an inner wall of the aortic arch around the at least one artery opening, and used to capture particles in blood flowing into the at least one artery opening. In further implementations, the mesh, frames and struts are collapsed with the captured particles therein, and the mesh, frames, struts and particles are retracted into the catheter which can then be removed.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIGS. 3A-3D show respective views of a catheter apparatus, in accordance with one or more example embodiments of the present disclosure;

FIGS. 7A-7G show respective views of a filter support manufacturing apparatus, in accordance with one or more example embodiments of the present disclosure;

Figure 1:
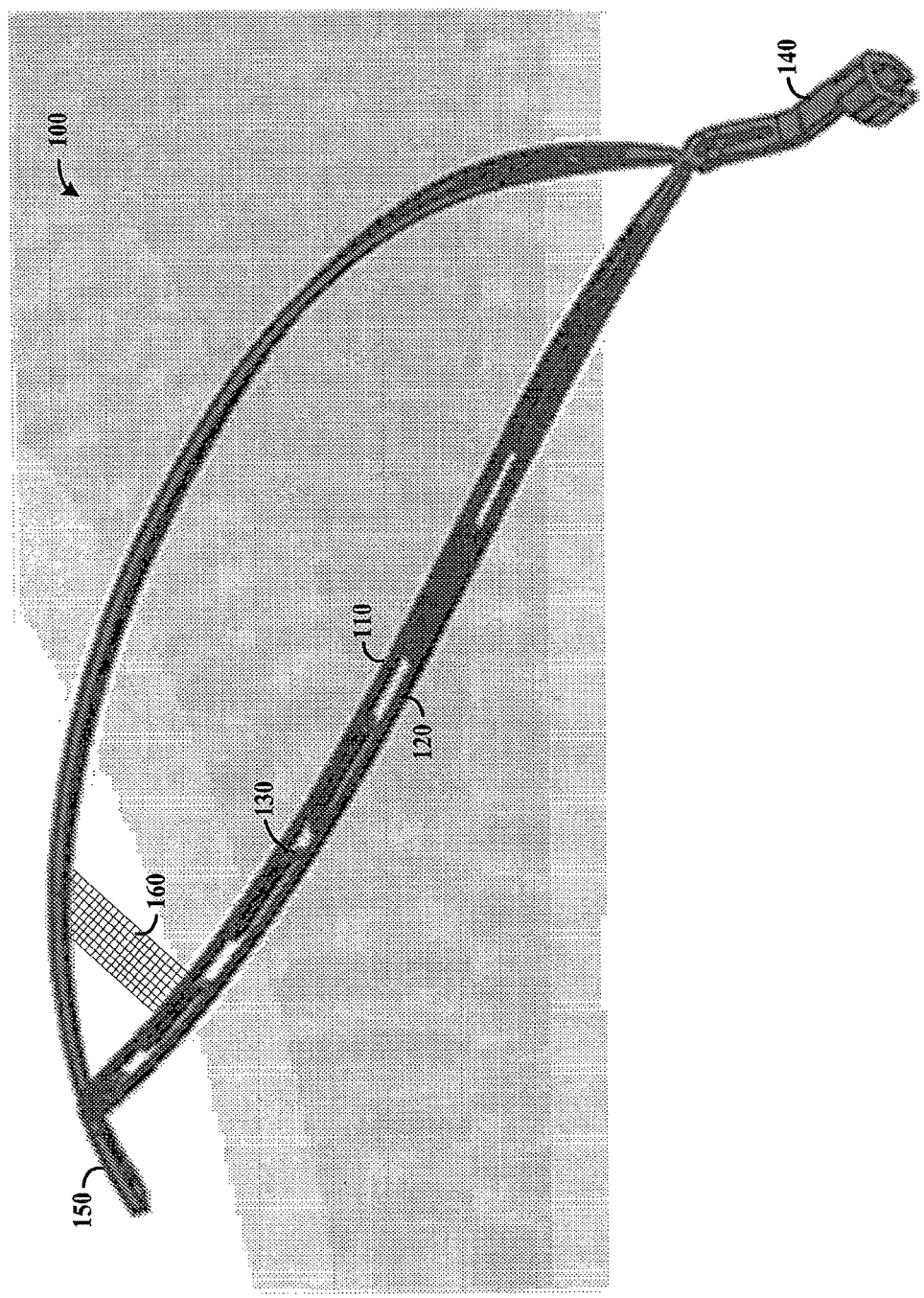
FIG. 1 shows a filter support apparatus, in accordance with one or more example embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving catheter-based apparatuses and methods. While not necessarily so limited, various aspects may be appreciated through a discussion of examples using this context.

Various example embodiments are directed to filtering blood flow into vascular tissue, which can be useful for trapping particulates while allowing the flow of blood. In a particular embodiment, an apparatus includes a catheter-deployed filter type membrane that filters particles from blood flow.

In particular embodiments, a filter apparatus mitigates or prevents embolus from traveling into the great vessels (Brachiocephalic/Innominate, Left Common Carotid, and Left Subclavian arteries), and may be implemented during surgery from the aortic arch, which is the portion of the main artery that bends between the ascending and descending aorta. The aortic arch leaves the heart and ascends, then descends back to create the arch. The aorta distributes blood from the left ventricle of the heart to the rest of the body, and exhibits variable flow characteristics, with hemodynamics of the aortic arch region often exhibiting a non-uniform distribution of pressure and velocity. Particles such as embolus can be filtered under such conditions, using a filter component that conforms to the variable geometry of the aortic arch during cyclic pressure variations, functioning as a filtering umbrella. The collected emboli is extracted and removed through a delivery tube to outside of the body, such as by collapsing and drawing the filter component into a sheath.

In a particular embodiment, a filter mechanism as noted above includes a main frame assembly (FA) and a mesh umbrella, attached securely to the frame. The frame and mesh may be integrated as a single piece/component or with two or more pieces/components. The FA operates to provide a mechanical seal about an opening in an inner wall of vascular tissue with the FA conformed to the wall. Accordingly, micro-emboli and other particulates can be prevented from entering the opening while allowing unrestricted blood flow within the vascular tissue to which the FA is conformed. In various implementations, the FA is operable to maintain the conformity and mechanical seal under variations in cyclic blood pressure for humans under various conditions including those involving surgery, and for various anatomies and conditions such as those involving variations in aortic arch diameter and/or size or the accumulation of plaque. For instance, a mesh may be deployed with an area that is at least twice as large as any opening or openings to be covered. As such, various aspects of the FA may be implemented to facilitate such capture during surgery via catheter deployment, with FA being operable to collapse/trap particulates such as micro-emboli and withdraw the particulates into the catheter for removal upon completion of the surgery. Moreover, by controlling pressure via mechanical spring force, the application of too much pressure can be avoided, as may be useful for instances in which vessel wall stiffening or aneurism may be present.

According to another example embodiment, an apparatus includes a catheter extending from a proximal end to a distal end, a shaft within and operable to move in the catheter, and a filter component connected to an end of the shaft and operable to extend from and retract within the distal end of the catheter. The filter component includes a mesh and inner and outer frames connected by struts, with the mesh is coupled to one or both of the inner frame and the outer frame. The outer frame extends along the inner frame (e.g., in a concentric type arrangement). The struts operate to apply a force between the outer frame and the inner frame, along a direction generally between the frames (tending to push the frames away from one another). The frames may be oval, round or rectangular, with the latter approach facilitating the implementation of a flat surface for applying pressure to tissue. One or more of the mesh, frames and struts can be made of a contiguous material. In various embodiments, the struts apply a force that presses the inner frame and mesh against tissue, such as against an inner region of vascular tissue. Brush-like structures can be used in a perimeter region to facilitate sealing.

As noted herein such approaches can be particularly useful for deploying the mesh against an inner wall of the aortic arch, sealing the mesh around one or more artery openings therein. Deployment may involve, for example, constraining movement of the filter assembly to rotational movement, via the catheter/shaft, which facilitates the application of pressure to the mesh against tissue walls. Further, these approaches can facilitate insertion and filtering while conforming nearly all of the mesh and supporting structure to a sidewall of the aortic arch, allowing blood to flow freely therein while also capturing particles that may otherwise enter the covered artery or arteries. For instance, human red blood cells can be passed while mitigating passage of particles having a dimension larger than the human red blood cells. These particles can be trapped within the mesh/frames such that they can be withdrawn without allowing the particles to further escape back into the bloodstream.

The mesh can be sealed to an interior vessel wall or other tissue in a variety of manners. In some embodiments, the struts operate with the inner frame, outer frame and mesh to, in a deployed state, seal a perimeter region of the mesh to an interior vessel wall by using an applied force to press the mesh perimeter region onto the interior vessel wall. This may involve, for example, applying a force along various struts and between different adjacent regions of the inner and outer frames, such that a distance between the frames varies relative to conformity of one or both frames to tissue anatomy. This flexibility allows the application of sufficient sealing force along the perimeter region, while also accommodating anatomical differences.

In various implementations, the mesh has opposing surfaces and is configured and arranged with the shaft, frames and struts to conform to an inner wall of vascular tissue and cover at least one opening in the vascular tissue. Substantially all of one of the opposing surfaces can be placed in contact with the wall or extending over the at least one opening. This facilitates placement of the mesh predominantly out of the flow of blood in the vascular tissue.

Deployment of the mesh, in these and other contexts, can be effected by the filter component, shaft and catheter by expanding the mesh in a first state in response to the filter component being extended out of the distal end of the catheter, and collapsing the mesh in a second state in response to the filter component being retracted into the catheter. Accordingly, the mesh can be collapsed for fitment into the catheter and expanded upon deployment with a much wider coverage for filtering (e.g., two or many more times the diameter of the catheter).

Forces may be translated the filter component in a variety of manners. In some embodiments, the filter component includes a mechanical spring coupled at the distal end of the shaft. The mechanical spring operates with the shaft and catheter as a base, to apply a spring force that directs the mesh against tissue. For instance, the mechanical spring may operate with the catheter and shaft to apply a spring force to the outer frame in a direction toward the inner frame, with the force being translated from the outer frame to the inner frame via the struts. In some implementations, the spring directly applies a force to the inner frame. The spring may be separate from, or integrated with, a support structure connecting the filter component to the shaft (or as part of the filter component). Such approaches can be used to apply the catheter within a human aortic arch, sealing the mesh to an inner wall of the aortic arch and therein covering at least one opening in the human aortic arch with mesh.

Mesh or other filter material as characterized herein may be implemented in a variety of manners. In some embodiments, a mesh includes a stiffening structure and is operable to fold and unfold in overlapping layers, respectively for retraction into the catheter and for deployment. The stiffening structure may, for example, include additional material on or in the mesh and regions that exhibit lower stiffness for folding. For instance, the mesh may be patterned with differently-sized pores and/or with pore density that facilitates longitudinal or lateral folding/stacking behavior. A spiral pattern can facilitate certain opening or closing behaviors. Areas with fewer or no pores can be implemented to induce a stiffening moment.

Turning now to the Figures, FIG. 1 shows an apparatus 100 as may be implemented for supporting a filter or mesh, in accordance with one or more example embodiments. The apparatus 100 includes an inner frame 110 and an outer frame 120 coupled by a struts 130 which operate to apply a force that pushes the inner and outer frame apart. A proximal end 140 is operable for coupling to a shaft, and is coupled to a distal end 150 via the frames. By way of example, the distal end 150 is shown extending at an angle relative to the inner frame 110, which can facilitate placement within a vessel wall (e.g., with the inner frame 110 pressed onto an inner wall within the aortic arch). Such an angle may facilitate placement of the apparatus into the aortic arch with the distal end 150 avoiding intervention into arteries in the walls. In certain implementations, a covering such as a thermoplastic show may be placed over the distal end 150 and facilitate interaction with vascular tissue.

In certain implementations, the proximal end 140 includes a mechanical spring (e.g., which may be integrated within the structure shown), that provides an upward (as depicted) spring force that can also facilitate pressing of the inner frame 110 against an inner wall of a vessel. For instance, with the proximal end 140 coupled to a shaft and inserted into vascular tissue via a catheter, the shaft and proximal end 140 can apply a spring force that tends to push the inner frame 110 upward and against an interior wall of the vascular tissue. Such an approach is particularly useful, for example, within an aortic arch. In some instances, both the frames are pressed against the inner wall of the vascular tissue. With a mesh coupled across the perimeter of the inner frame 110 (and, in some instances, across an overlying perimeter of the outer frame 120), blood flowing through openings in the inner wall within the perimeter of the inner frame is thus filtered via the mesh. Such a mesh may, for example, be implemented with a structure as shown at 160 (partially shown, with such a mesh filling the entire interior area within the perimeter of the inner frame 110). Moreover, a spring force in the proximal end 140 can be used to maintain a seal against a vessel wall under various blood flow conditions and for various anatomies.

In various implementations, mechanical force applied via such a spring and/or the struts 130 may be implemented as a primary force that conforms the structure against the inner wall (e.g., with a mechanical force that is many times larger than fluidic force of blood passing through a vessel). This force may be tuned, for example, during a manufacturing process to tailor the application to a particular use. For instance, the force can be scaled based on a patient's age and condition of the wall against which the mesh is to be deployed, such as may relate to size or the presence of plaque. Controlling an adherence force can facilitate optimization of the size of the mesh, such that the mesh need not be oversized to compensate for any such force.

The apparatus 100 may be made of one or more components. In some embodiments, the inner frame 110, outer frame 120 and struts 130 are formed of a contiguous material, eliminating any need for joints. In various implementations, a mesh (e.g., 160) coupled across the inner frame 110 is also formed with at least the inner frame of a contiguous material. For example, a contiguous nitinol material may be used to form one or all of the components in the apparatus 100. In some embodiments, a thin thermoplastic material is used a mesh and coupled to the inner frame. Where two components are used, they may be joined together using joining methods involving one or more of heat and pressure, adhesive, and lasers. The frames and struts can also be made using polymeric material and/or metallic material. The mesh can be attached directly to the frames and/or to itself.

In various embodiments, a mesh such as mesh 160 includes brush like teeth and grooves that enhance the grip of the mesh over rough terrain (e.g., over the surface of the aortic arch). These brush features may be located in the area of the frames. Small features such as microfeatures (relative to the vessel wall structures) receive the spring force and are highly compressible against the vessel, therein sealing against the vessel.

In various implementations, the apparatus 100 is operable to keep tissue under tension (e.g., along and into the interior of vascular tissue) when the inner and outer frames 110/120 are deployed. In this context, enough sealing pressure is applied to maintain the structure sealed against the wall under conditions in which blood is flowing past and through the mesh. This involves providing a smooth surface of interaction along an interface between the apparatus and the surface of the tissue (e.g., of the aortic arch). Such an approach can be implemented with few or no bumps or raised sections due to welding, bonding, overlap, and reducing/minimizing features such as "gutters," thus facilitating a tight seal with the vascular tissue.

Figure 2:
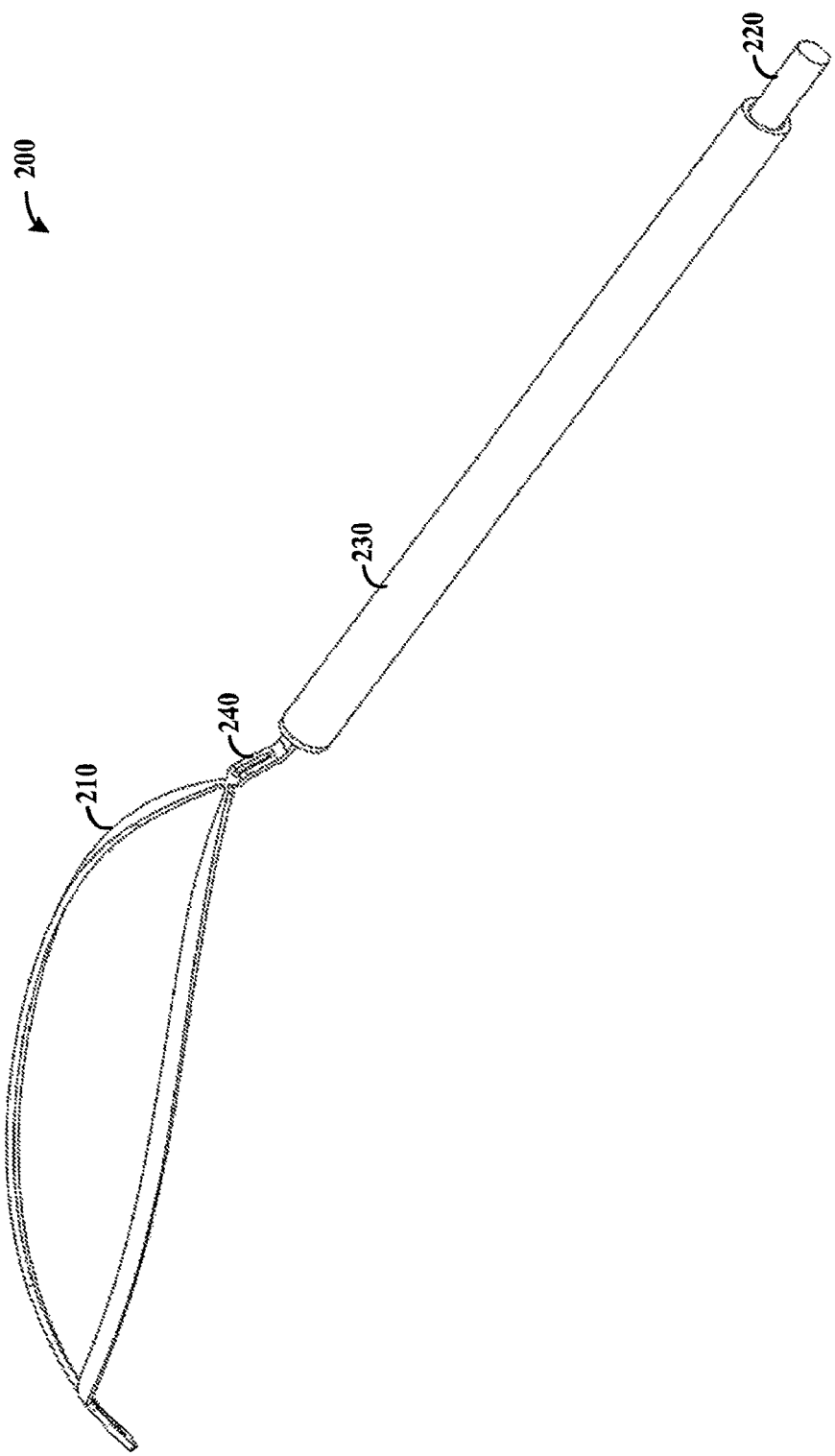
FIG. 2 shows a catheter apparatus, in accordance with one or more example embodiments of the present disclosure.

FIG. 2 shows an apparatus 200, in accordance with one or more example embodiments of the present disclosure. The apparatus 200 includes a filter component 210, which may be implemented with inner and outer frames with connecting struts as shown in FIG. 1. The filter component is connected to a shaft 220 that extends through a catheter 230 (e.g., with the shaft and catheter being many times longer than the portions shown). A proximal end 240 of the filter component 210 is secured to the shaft 220 and provides a spring force an in upward direction as depicted in the figure, sealing a perimeter of the filter component 210 against a vessel wall when deployed therein.

FIGS. 3A-3D show respective views of an apparatus 300, in accordance with one or more example embodiments of the present disclosure. As shown in FIG. 3A, the apparatus 300 includes a filter component 310 coupled to a shaft 320 within a catheter 330, with the filter component being retractable into the catheter. A mesh may be coupled to and/or integrated with the filter component 310, across respective rails (e.g., as shown in FIG. 1). FIG. 3B shows a cross-sectional view "A-A" from FIG. 3A, with FIG. 3C showing a view of a distal end of the catheter and shaft as coupled to a proximal end 340 of filter component 310. In various implementations, a portion of the proximal end 340 is locked in place onto the shaft 320 such that it does not extend beyond end 350 of the catheter 330. This maintains componentry within the catheter and out of the bloodstream when deployed in vascular tissue. FIG. 3D shows an alternate view of the apparatus 300.

In various implementations, a portion of the proximal end 340 is locked in place onto the shaft 320 such that it does not extend beyond the end of the catheter 330. This maintains componentry within the catheter and out of the bloodstream when deployed in vascular tissue.

Figure 4:
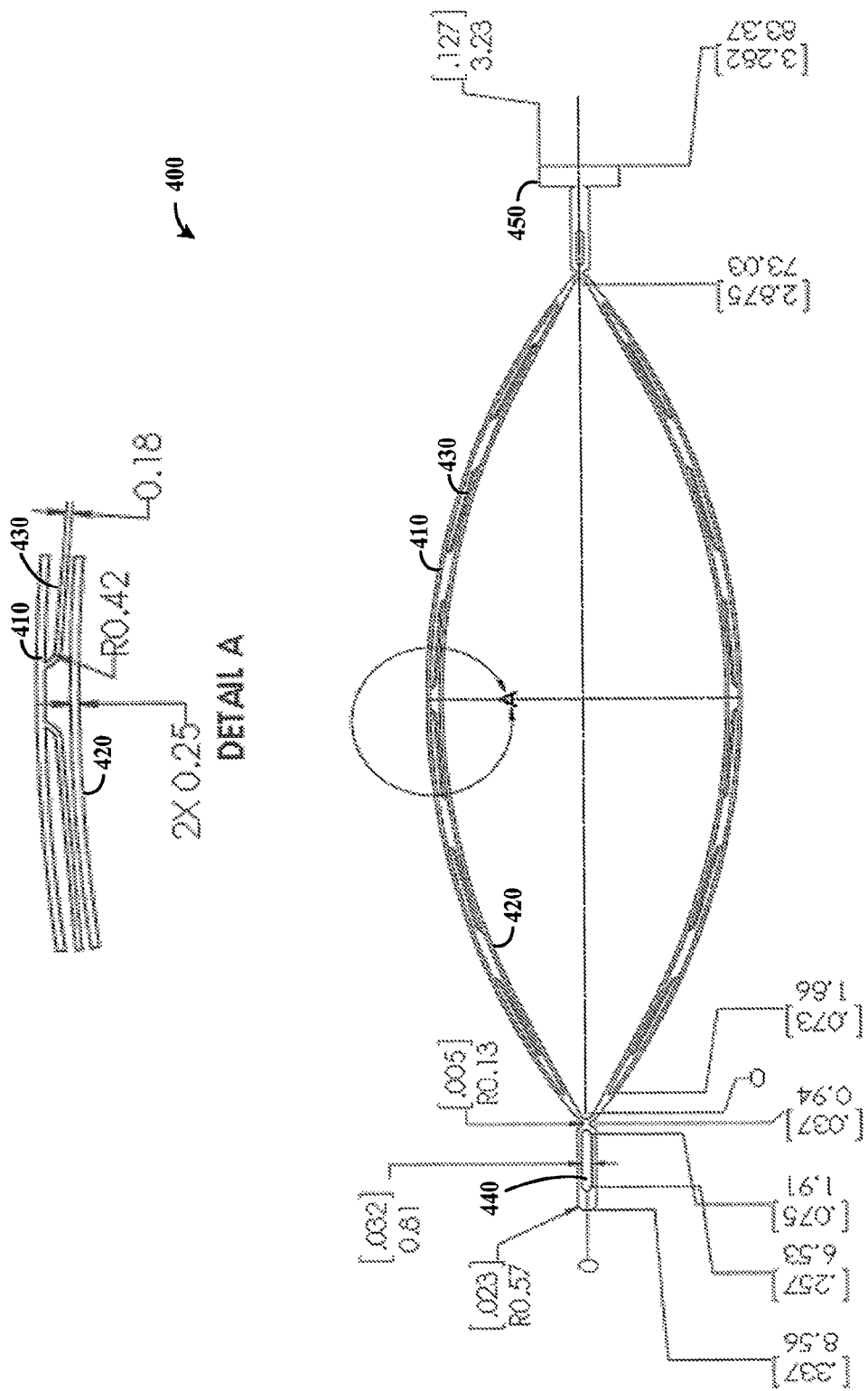
FIG. 4 shows a filter support apparatus, in accordance with one or more example embodiments of the present disclosure.

FIG. 4 shows an apparatus 400 as may be implemented to support a mesh or filter, in accordance with one or more example embodiments of the present disclosure. The dimensions shown in FIG. 4 are exemplary, as may be implemented for certain embodiments. The apparatus 400 includes an inner frame 410, outer frame 420 and struts 430 that push the frames apart. Detail "A" provides an exemplary view of these components. A distal end 440 and proximal end 450 are coupled to the frames as shown.

Figure 5:
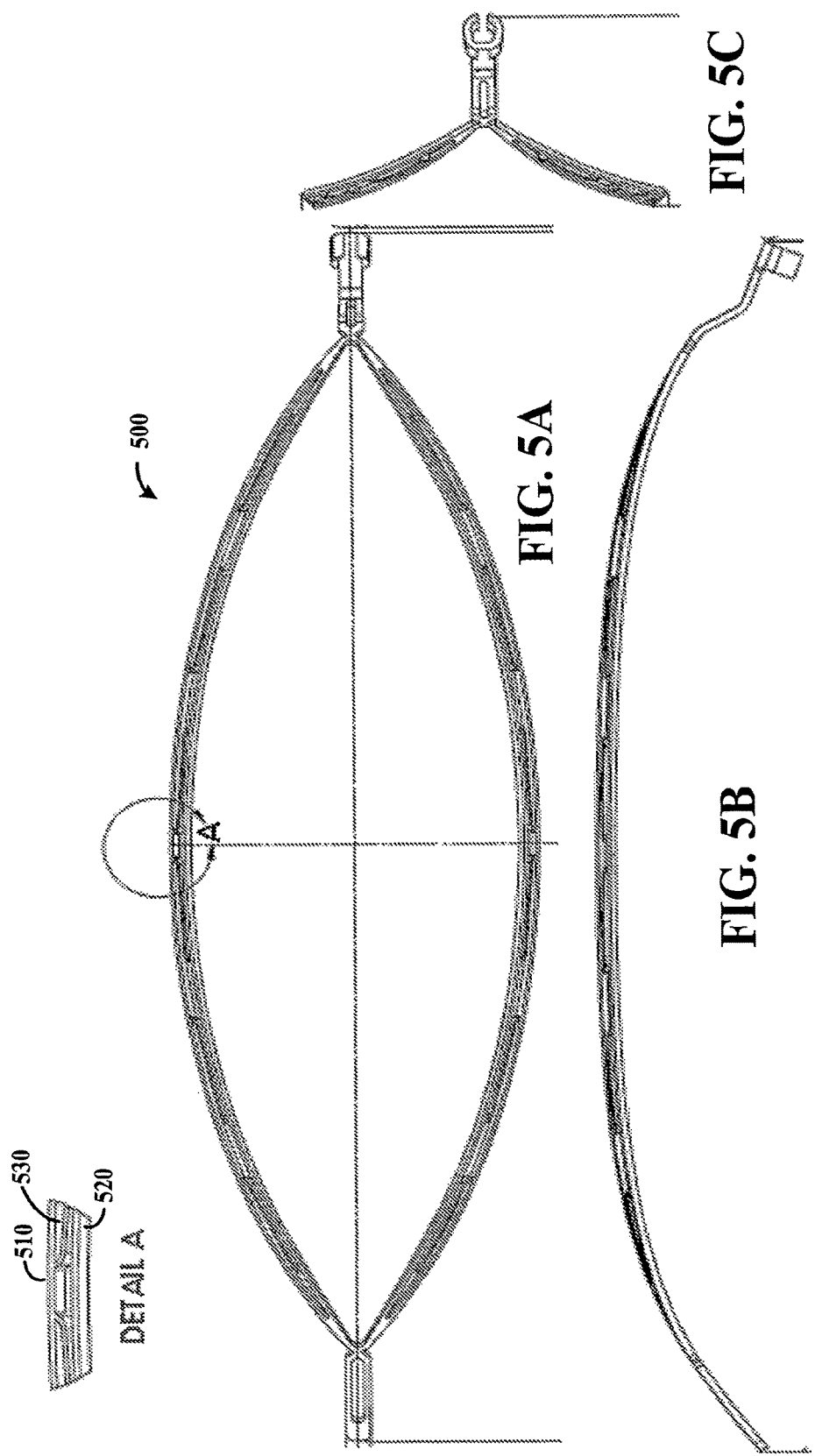
FIGS. 5A-5C show respective views of a filter support apparatus, in accordance with one or more example embodiments of the present disclosure.

FIGS. 5A-5C show respective views of an apparatus 500 as may be implemented to support a mesh or filter, in accordance with one or more example embodiments of the present disclosure. The apparatus 500 may be implemented similarly to that shown in FIG. 4. As noted in the detail portion "A" of FIG. 5A, inner (510) and outer (520) frames are connected by struts 530 that push the inner frame away from the outer frame and onto a vessel wall. FIGS. 5B and 5C respectively show side and end views of the apparatus 500.

Figure 6:
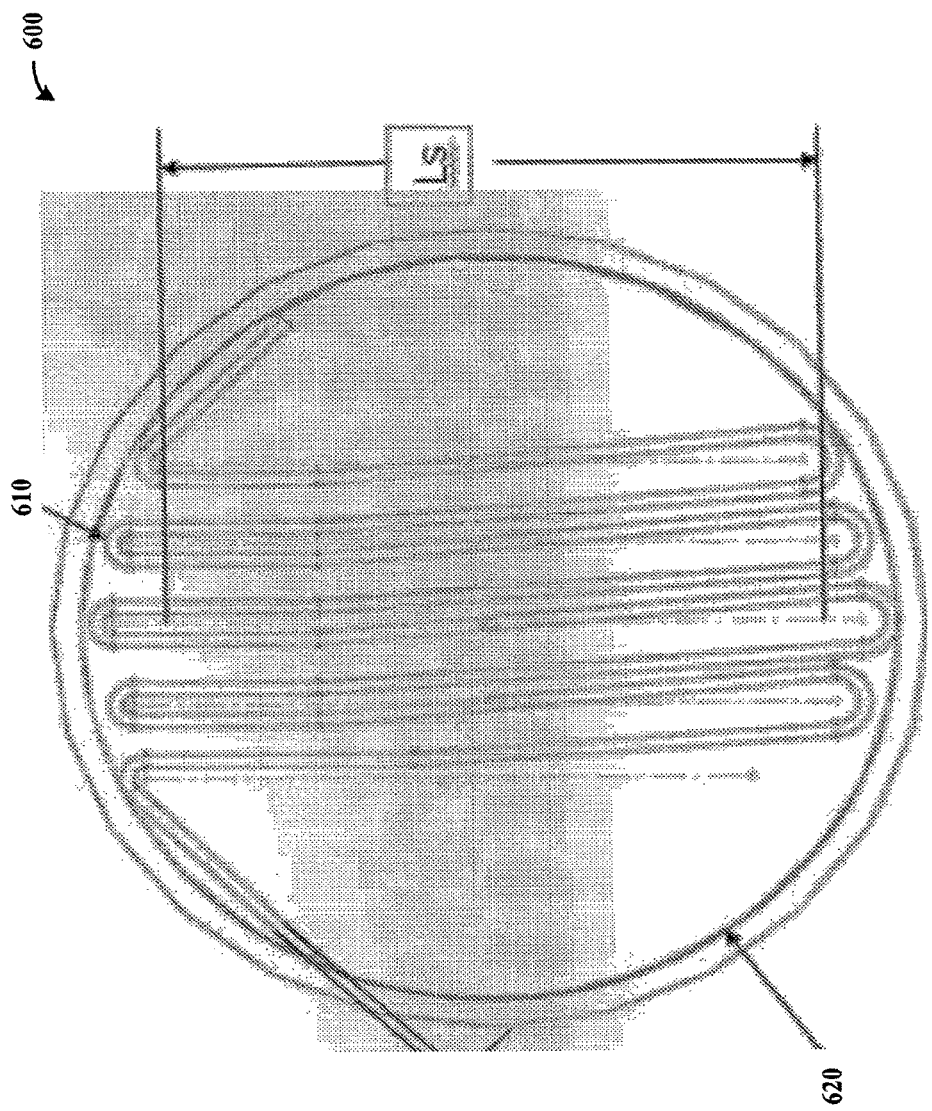
FIG. 6 shows a catheter apparatus with a retracted mesh, in accordance with one or more example embodiments of the present disclosure.

FIG. 6 shows a catheter apparatus 600 with a retracted mesh 610 within a sheath 620, in accordance with one or more example embodiments of the present disclosure. The mesh 610 may, for example, be implemented with filter components as shown in FIGS. 1 and 2, and operable for folding and retraction into a catheter. For instance, after deployment upon a an inner wall of the aortic arch and use for filtering particulates from blood flowing into arteries sealed by the mesh 610, the mesh can be folded and retracted into the sheath 620 as shown to trap and remove the particulates. In various implementations, the mesh 610 has stiffening/ribs structure which enables it to fold and unfold in certain desired direction when it is deployed or retracted within the sheath 620.

Figure 7A:
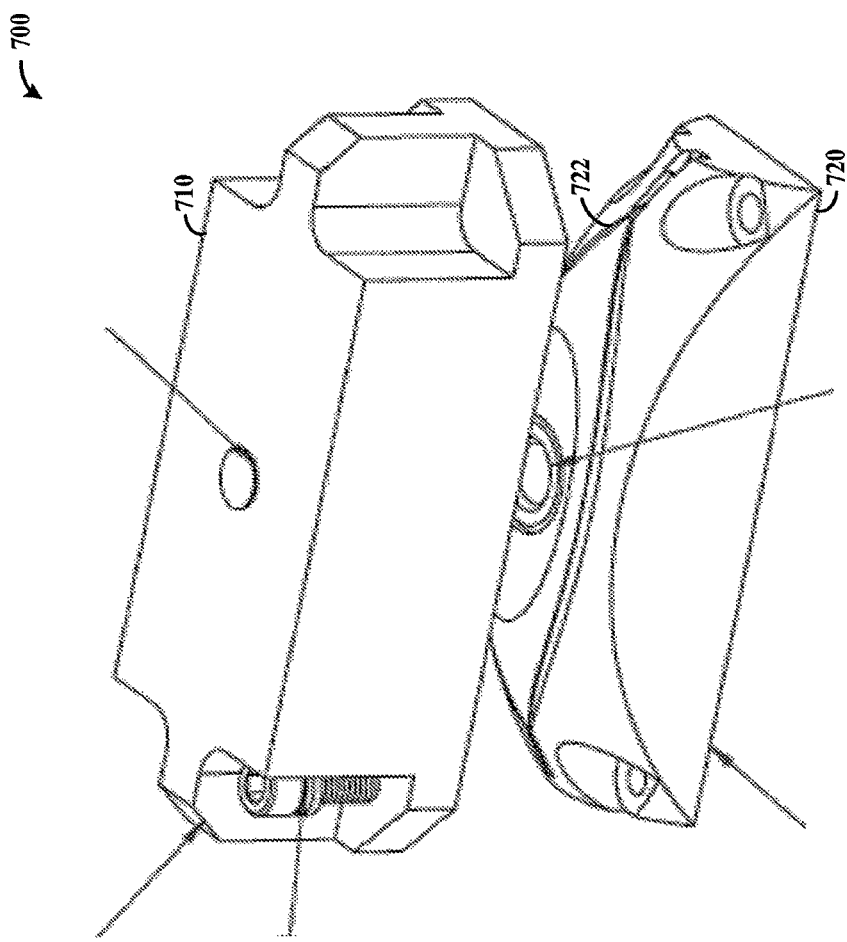

FIGS. 7A-7G show respective views of a filter support manufacturing apparatus 700, as may be implemented in accordance with one or more example embodiments of the present disclosure. The respective dimensions shown are exemplary, with the understanding that the apparatus 700 may be built to a variety of dimensions. The apparatus 700 may, for example, be used to manufacture one or more filter components as shown in other figures herein. Referring to FIG. 7A, an upper fixture 710 and lower fixture 720 are shown in perspective view, with a formed region 722 shown on the lower fixture and operable for forming a filter component.

FIGS. 7B and 7C respectively show end and top views of the apparatus 700, with the upper and lower fixtures 710 and 720 positioned in a forming stage. Section A-A from FIG. 7B is also shown with a region 730 providing a space between the upper and lower fixtures 710/720 for forming the filter component. Such an approach can be facilitated for a variety of molding approaches.

FIG. 7D and FIG. 7E respectively show top and perspective views of the lower fixture 720. As part of FIG. 7D, sections A-A, B-B, D-D and detail C are shown for various cross sections and related detail. Region 730 is recessed for forming part of a filter component.

FIG. 7F and FIG. 7G respectively show top and perspective views of the upper fixture 710. As part of FIG. 7F, sections A-A and B-B are shown for respective cross sections. Region 740 is recessed for forming part of a filter component.

Various other approaches to manufacturing may be implemented to suit particular embodiments. In some embodiments, a starting material is processed to generate a mesh. For example, in some instances a flat nitinol material is used, in which a mesh area is first reduced to less than 0.005" (or less than 0.001") using electro-discharge machining (EDM) or other technique. The frame assembly and mesh patterns are then cut using for example a laser. In some instances, the order of process is reversed such that a frame assembly (frames) are laser cut followed by EDM and laser patterning.

In various embodiments, a frame assembly such as may be implemented with the frame/mesh supporting components shown in one or more of FIGS. 1-5C has a rectangular cross section that provides directional stiffness and also higher force relative to a circular cross section. The rectangular cross section provides a desirable surface contact area and more distributive force, which facilitates sealing. The flat and rectangular frame structure can be implemented with a double frame and struts to keep tissue under tension (no sagging) in both lateral and axial directions. This can facilitate uniform fluid pressure on the mesh and artery openings in the tissue.

Figure 8:
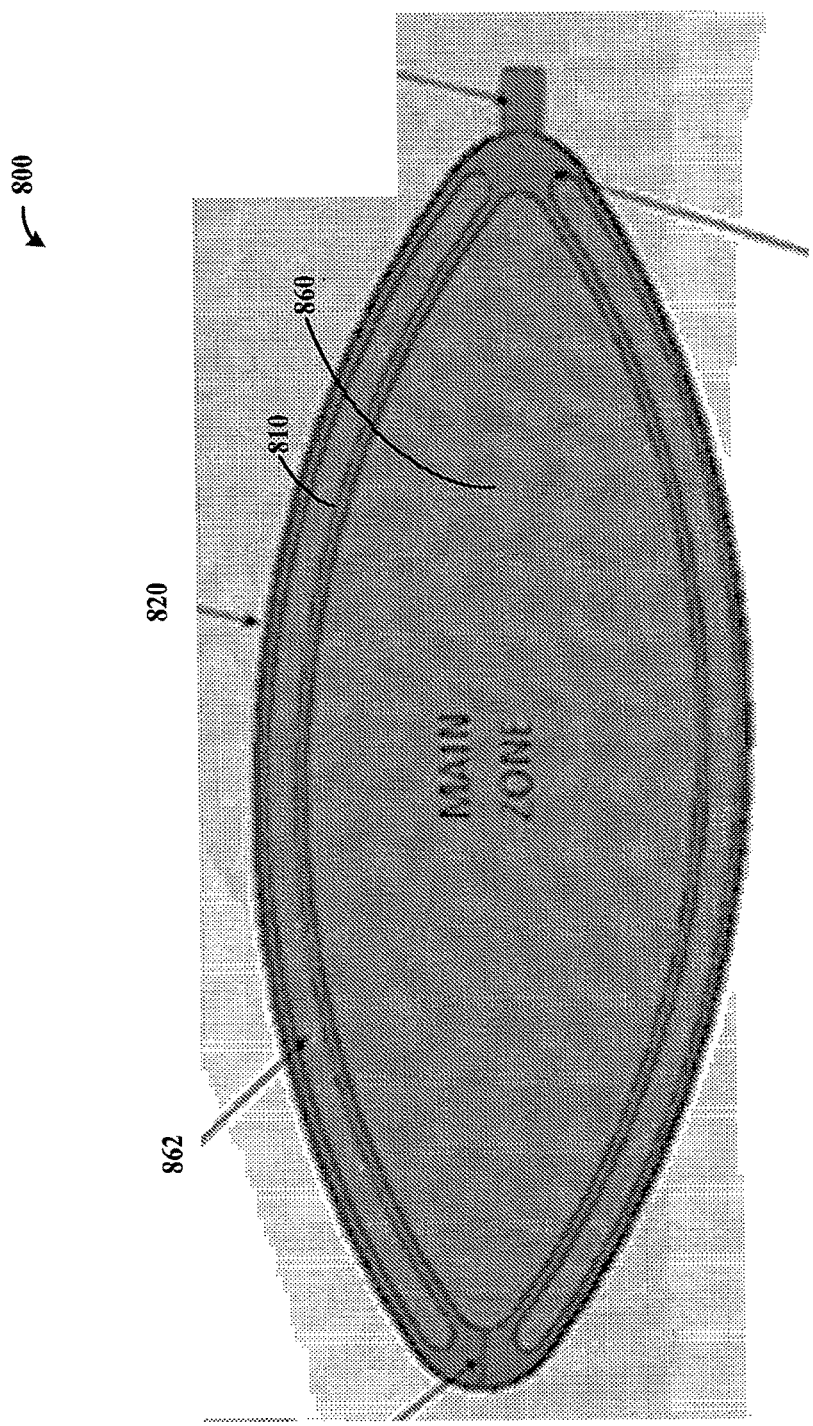
FIG. 8 shows a filter component, as may be implemented with various embodiments.

Referring to FIG. 8, an apparatus 800 is shown, as may be implemented with various embodiments involving filtering. The apparatus 800 includes inner and outer frames 810 and 820, and a mesh 860 that covers a main zone within a perimeter defined by the inner frame and in a region 862 between the inner and outer frames. In various embodiments, two mesh layers are implemented, with a first mesh having a perimeter that aligns with the perimeter of the inner frame 810 a second mesh overlying the first mesh and having a perimeter that aligns with the perimeter of the outer frame 820. In various embodiments, the inner frame 810 and outer frame 820 are operable for pressing against the inner wall of vascular tissue, forming a flat or double seal for filtering blood flowing through an artery in the inner wall. The apparatus 800 may also be implemented with struts between the inner and outer frame, such as shown in FIG. 4.

In various embodiments, a frame assembly is designed to provide spring constant(s) of frame assembly with double flat seal around the main zone. This can increase the reliability of the sealing, provide increased contact force to interior walls of tissue (e.g., aorta) and more adhesion/bonding force between the tissue and the layers. The frame structure may be implemented with spring componentry that facilitates deployment and collapse of the mesh. The frame assembly may be made of four layers to support forces for sealing, deployment, lateral, twisting, pull-in, and constraint. These aspects may, for example, be implemented with the apparatus 800 in FIG. 8 as well as other filter componentry as shown in the other figures.

Figure 9:
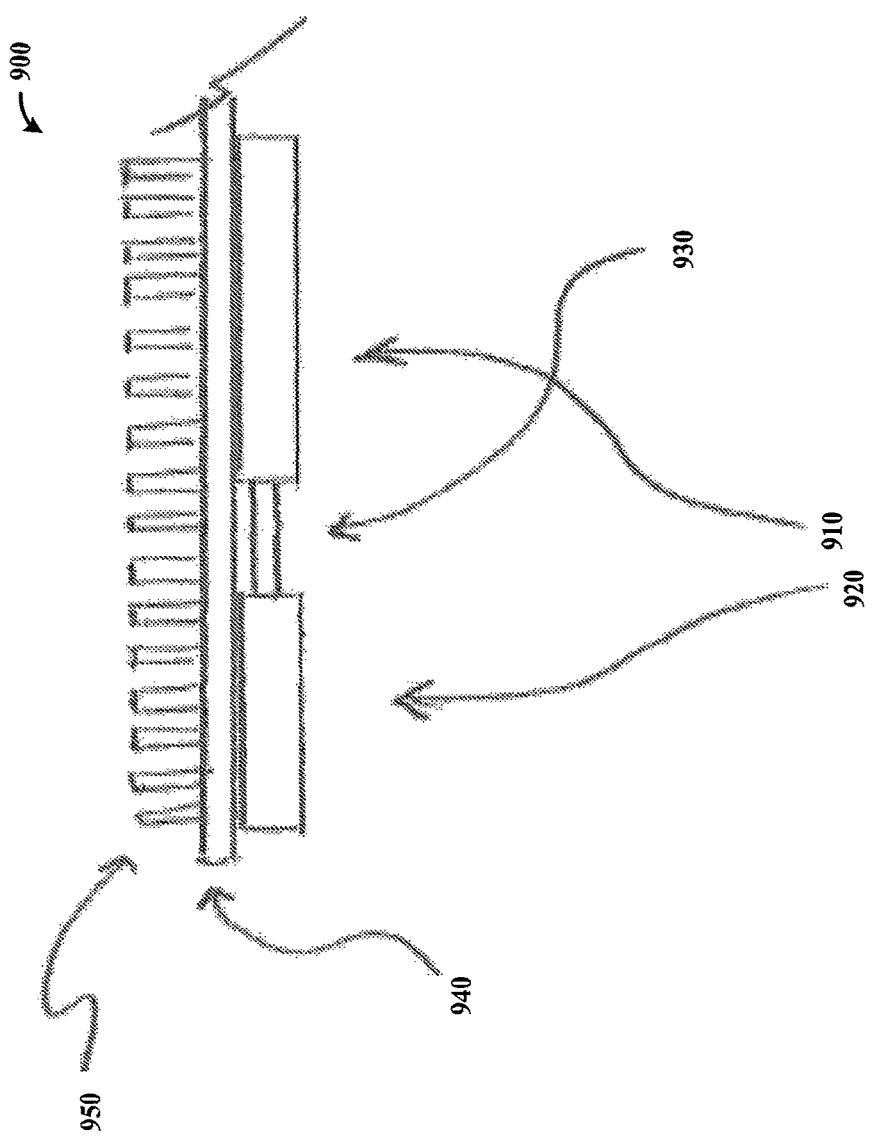
FIG. 9 shows brush features of an apparatus as may be implemented with one or more embodiments.

FIG. 9 shows brush features of an apparatus 900 as may be implemented with one or more embodiments. For instance, the features shown in FIG. 9 may be implemented with the mesh 160 in FIG. 1. The apparatus 900 includes inner and outer frames 910 and 920, coupled by struts 930 that tend to push the frames away from one another. A mesh 940 (a portion shown) is coupled to the frames and brush-like features 950 are coupled to the mesh near the frames. The frames 910 and 920 together with the struts 930 apply pressure to the mesh 940 and to the brush-like features 950 in an upward direction as depicted in the figure, such as for sealing the mesh to an inner wall of vascular tissue (e.g., over an surface of the aortic arch). The brush-like features 950, which may be formed of a common material with the mesh 940, are compressible for facilitating sealing of the mesh against an inner wall.

Based upon the above discussion and illustrations, those skilled in the art will readily recognize that various modifications and changes may be made to the various embodiments without strictly following the exemplary embodiments and applications illustrated and described herein. For example, different types of materials may be used for the various components herein, and other manners in which to expand/collapse mesh-type structures with similar effect can be implemented. Additional and/or differently-shaped frame portions or struts may be used to tailor the application to particular anatomies. In addition, the various methods described herein may be implemented with different types of arteries, valves and tissue, as well as different types of live beings. Such modifications do not depart from the true spirit and scope of various aspects of the invention, including aspects set forth in the claims.

What is claimed is:

1. An apparatus comprising:
 a catheter extending from a proximal end to a distal end;
 a shaft extending in the catheter from the proximal end to the distal end and being configured and arranged to move within the catheter; and
 a filter component connected to the shaft and configured and arranged to retract within the distal end, the filter component including
 a mesh,
 an inner frame having a perimeter,
 an outer frame having a perimeter extending around the perimeter of the inner frame, wherein the mesh extends within the perimeter of the inner frame and between the inner frame and the outer frame, and
 a plurality of struts that couple the inner frame to the outer frame, each strut extending lengthwise from a first end connected to and terminating on the inner frame, to a second end connected to and terminating on the outer frame, the struts being configured and arranged to apply a force between the outer frame and the inner frame, wherein the shaft, inner frame, outer frame and struts are configured and arranged to seal an opening in an interior vessel wall with the mesh by pressing the mesh and the inner and outer frames against the interior vessel wall and around the opening.

2. The apparatus of claim 1, wherein the struts are configured and arranged with the inner frame, outer frame and mesh to, in a deployed state, seal a perimeter of the mesh around the opening in the interior vessel wall by translating the applied force between the perimeter of the inner frame and the perimeter of the outer frame to press the mesh perimeter onto the interior vessel wall.

3. The apparatus of claim 2, wherein the filter component is configured and arranged with the shaft and catheter to
 expand the mesh in a first state in response to the filter component being extended out of the distal end of the catheter, the mesh having a dimension in the first state that is wider than a cross-sectional area of the catheter, and
 collapse the mesh in a second state in response to the filter component being retracted into the catheter.

4. The apparatus of claim 1, wherein the filter component is configured and arranged to trap particulates in contact with the mesh by collapsing the mesh and the frames.

5. The apparatus of claim 1, wherein the filter component includes a mechanical spring coupled at the distal end of the shaft, the mechanical spring being configured and arranged with the catheter and shaft to apply a spring force to the outer frame in a direction toward the inner frame.

6. The apparatus of claim 1, wherein the filter component includes an integrated spring at the distal end of the shaft, the integrated spring being configured and arranged with the catheter and shaft to apply a spring force through the outer frame, struts and inner frame, and with the catheter deployed within a human aortic arch, that seals the mesh to an inner wall of the aortic arch, therein covering at least one opening in the human aortic arch with mesh.

7. The apparatus of claim 1, wherein the mesh and the inner frame include a continuous material.

8. The apparatus of claim 1, wherein the mesh is configured and arranged to pass human red blood cells and to mitigate passage of particles having a dimension larger than the human red blood cells.

9. The apparatus of claim 1, wherein the filter component includes a proximal end connected to the shaft and a distal end coupled to the proximal end via the inner and outer frames, the distal end having a flat surface portion extending from the inner and outer frames at an angle relative to a direction along the shaft.

10. The apparatus of claim 1, wherein the mesh includes a plurality of brush features configured and arranged to grip the surface of an interior vessel wall.

11. The apparatus of claim 1, wherein the inner frame has a rectangular cross section configured and arranged with a surface thereof in contact with the mesh and configured and arranged therewith to engage the surface with the mesh thereupon with an interior vessel wall, therein sealing the mesh to the vessel wall.

12. The apparatus of claim 1, wherein the mesh is configured and arranged with a stiffening structure and to fold and unfold in overlapping layers, respectively for retraction into the catheter and for deployment.

13. The apparatus of claim 1, wherein a portion of the filter component connected to the shaft is configured and arranged with the catheter and shaft to remain within the catheter while the mesh, inner frame, outer frame and struts are deployed.

14. The apparatus of claim 1, wherein the filter component is fixed to the shaft and is constrained in movement to rotation relative to the catheter.

15. The apparatus of claim 1, wherein the catheter is configured and arranged for insertion into a human aortic arch, and the shaft and filter component are configured and arranged to conform the filter component to an interior wall of the aortic arch and to cover an opening in the aortic arch leading into at least one artery, with the struts pressing the mesh and the inner frame against an inner wall of the aortic arch and around the opening in the aortic arch leading into the at least one artery.

16. The apparatus of claim 1, wherein the mesh has opposing surfaces and is configured and arranged with the shaft, frames and struts to conform to an inner wall of vascular tissue and to cover at least one opening therein, with substantially all of one of the opposing surfaces being in contact with the wall or extending over the at least one opening with portions of the mesh being in contact with the wall adjacent the at least one opening.

17. The apparatus of claim 1, wherein
the perimeters of the inner frame and the outer frame form respective enclosed loops with the enclosed loop of the outer frame extending around the enclosed loop of the inner frame,
the mesh has a perimeter that is coupled to the outer frame, the perimeter defining a continuous surface area that is enclosed by the outer frame, and
the struts include respective struts extending from different locations around the perimeter of the inner frame, along respective lengths of the perimeters of the inner and outer frames, to corresponding locations around the perimeter of the outer frame, and are configured and arranged with the inner frame, outer frame and mesh to, in a deployed state, seal a portion of the surface area of the mesh around the opening in the interior vessel wall with the inner frame by translating the applied force from the outer frame to the inner frame.

18. The apparatus of claim 17, wherein the outer frame is configured and arranged to form a second seal around the opening in the interior vessel wall by sealing the perimeter of the mesh around the opening in the interior vessel wall and around the portion of the surface area of the mesh sealed around the opening by the inner frame.

* * * * *